United States Patent
Barley, Jr. et al.

(10) Patent No.: US 6,492,434 B1
(45) Date of Patent: *Dec. 10, 2002

(54) METHODS FOR INHIBITING SKIN ULCERATION BY USE OF CYANOACRYLATE ADHESIVES

(75) Inventors: Leonard V. Barley, Jr., Colorado Springs, CO (US); Michael M. Byram, Colorado Springs, CO (US); Patrick J. Tighe, Littleton, CO (US); Richard J. Greff, Yorba Linda, CA (US)

(73) Assignee: Flowers PArk Ltd., Cheshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/393,019

(22) PCT Filed: Jun. 23, 1994

(86) PCT No.: PCT/US94/07153

§ 371 (c)(1),
(2), (4) Date: Feb. 27, 1995

(87) PCT Pub. No.: WO95/00153

PCT Pub. Date: Jan. 5, 1995

(51) Int. Cl.$^7$ .......................... C08K 6/08; A61K 31/74; A61K 37/785
(52) U.S. Cl. ................. 523/118; 424/78.35; 424/78.02; 424/445; 514/925; 514/928
(58) Field of Search .................. 424/78.35; 523/118

(56) References Cited

U.S. PATENT DOCUMENTS

| | | | |
|---|---|---|---|
| 2,804,073 A | 8/1957 | Galliene et al. | 128/156 |
| 3,527,224 A | 9/1970 | Rabinowitz | 526/297 |
| 3,591,676 A | 7/1971 | Hawkins et al. | 424/78.06 |
| 3,667,472 A | 6/1972 | Halpern | |
| 3,995,641 A | 12/1976 | Kronenthal et al. | 558/400 |
| 4,035,334 A | 7/1977 | Davydov et al. | 424/78.06 |
| 4,287,177 A | 9/1981 | Nakashima et al. | 424/81 |
| 4,444,933 A | 4/1984 | Columbus et al. | 524/292 |
| 4,650,826 A | 3/1987 | Waniczek et al. | |
| 4,958,748 A | 9/1990 | Otake | |
| 5,270,168 A | 12/1993 | Grinnell | 435/7.21 |
| 5,306,490 A * | 4/1994 | Barley, Jr. | 424/78.35 |

FOREIGN PATENT DOCUMENTS

JP  587717 A  9/1983

OTHER PUBLICATIONS

Galil et al Journal of Biomed. Mater. Res. vol. 18 601–607.*
Akers et al Arch. Derm. vol. 107 4/'73.*
Bhaskar, Surindar N. et al., "Healing of Skin Wounds with Butyl Cyanoacrylate", pp 294–297, 1969, Journal of Dental Research, vol. 48, No. 2.
Dalvi, A. et al., "Non–suture Closure of Wound Using Cyanoacrylate", pp 97–100, 1986, Journal of Postgraduate Medicine, vol. 32, No. 2.
Eiferman, Richard A. et al., "Antibacterial Effects of Cyanoacrylate Glue", pp 958–960, Jun. 1983, Archives of Ophthalmology, vol. 101.
Ellis, David A.F. et al., "The Ideal Tissue Adhesive in Facial Plastic and Reconstructive Surgery", pp 68–72, 1990, The Journal of Otolaryngology, vol. 19, No. 1.
Fung, Ramona Q. et al., "Use of Butyl–2–Cyanoacrylate in Rabbit Auricular Cartilage", pp 459–464, Jul. 1985, Archives of Otolaryngology, vol. 111.
Galil, K.A. et al., "The Healing of Hamster Skin Ulcers Treated with N–butyl–2–cyanocrylate (Histoacryl blue)", pp 601–607, 1984, Journal of Biomedical Materials Research, vol. 18.
Harper, Marion C., "Stabilization of Osteochondral Fragments Using Limited Placement of Cyanoacrylate in Rabbits", pp 272–276, Jun. 1988, Clinical Orthopaedics and Related Research 231.
Kamer, Frank M. et al., "Histoacryl: Its Use in Aesthetic Facial Plastic Surgery", pp 193–197, Feb. 1989, Archives of Otolaryngology Head and Neck Surgery, vol. 115.
Kosko, Paul I., "Upper Lid Blepharoplasty: Skin Closure Achieved with Butyl–2–Cyanoacrylate", pp 424–425, Jun. 1981, Ophthalmic Surgery, vol. 12.
Makady, F. M. et al., "Effect of tissue adhesives and suture paterns on experimentally induced teat lacerations in lactating dairy cattle", pp 1932–1934, Jun. 1991, JAVMA, Reports of Original Studies, vol. 198, No. 11.
Matsumoto, Teruo, "Bacteriology and Wound Healing", pp 106–113, 1972, Chapter 3 in Tissue Adhesives in Surgery.
Matsumoto, Teruo, "Clinical Considerations and Applications of Bucrylate Tissue Adhesive", pp 226–237, 1972, Tissue Adhesives in Surgery, Chap. 1, Sec. III.
Matsumoto, Teruo, "Reactions of the Organism to Acrylate–Adhesives", pp 436–444, 1972, Tissue Adhesives in Surgery.
Matsumoto, Teruo et al., "Tissue Adhesive and Wound Healing", pp 266–271, Mar. 1969, Archives of Surgery, vol. 98.
Mizrahi, S. et al., "Use of Tissue Adhesives in the Repair of Lacerations in Children", pp 312–313, Apr. 1988, Journal of Pediatric Surgery, vol. 23, No. 4.
Morton, R.J. et al., "The Use of Histoacryl Tissue Adhesive for the Primary Closure of Scalp Wounds", pp 110–112, 1988, Archives of Emergency Medicine, vol. 5.

(List continued on next page.)

Primary Examiner—Thurman K. Page
Assistant Examiner—Blessing Fubara
(74) Attorney, Agent, or Firm—Burns, Doane, Swecker & Mathis, L.L.P

(57) ABSTRACT

A cyanoacrylate adhesive is applied onto intact surface skin areas prone to ulceration so as to inhibit formation of surface skin ulcers.

13 Claims, No Drawings

OTHER PUBLICATIONS

Ousterhout, D.K. et al., "Cutaneous Absorption of n–Alkyl–a–Cyanoacrylate", pp 157–163, 1968, Journal of Biomedical Materials Research, vol. 2.

Pepper, D.C., "Kinetics and Mechanism of Zwitterionic Polymerization of Alkyl Cyanoacrylate", pp 629–637, 1980, Polymer Journal, vol. 12, No. 9.

Pepper, David Charles et al., "Kinetics of Polymerization of Alkyl Cyanoacrylate by Tertiary Amines and Phosphines", pp 395–410, 1983, Makromol. Chem., vol. 184.

Ronis, Max L. et al., "Review of Cyanoacrylate Tissue Glues with Emphasis of Their Otorhinolaryngological Applications", pp 210–213, Feb. 1984, Laryngoscope., vol. 94.

Saches, Michael Evan., "Enbucrylate as Carilage Adhesive in Augmentation Rhinoplasty", pp 389–393, Jun. 1985, Archives of Otolaryngology, vol. 111.

Toriumi, Dean M. et al., "Histotoxicity of Cyanoacrylate Tissue Adhesives: A Comparative Study", pp 546–550, Jun. 1990, Archives of Otolaryngology Head and Neck Surgery, vol. 116.

Tseng, Yin–Chao et al., "Modification of Synthesis and Investigation of Properties for 2–cyanoacrylate", pp 73–79, Jan. 1990, Biomaterials, vol. 11.

Vinters, H.V. et al., "The Histotoxicity of Cyanoacrylate: A Selective Review", pp 279–291, 1985, Neuroradiology, vol. 27.

Watson, David P., "Use of Cyanoacrylate Tissue Adhesive for Closing Facial Lacerations in Children", p 1014, Oct. 1989, British Medical Journal, vol. 299.

* cited by examiner

METHODS FOR INHIBITING SKIN ULCERATION BY USE OF CYANOACRYLATE ADHESIVES

CROSS-REFERENCE TO RELATED APPLICATIONS

This application is derived from International Application Serial No. PCT/US94/07153 which claims priority to U.S. patent application Ser. No. 08/082,927, now U.S. Pat. No. 5,403,591.

BACKGROUND OF THE INVENTION

1. Field of the Invention

This invention is directed to methods for inhibiting the formation of surface skin ulcers by using cyanoacrylate adhesives. The cyanoacrylate adhesive to be used can be stored in dispensers for single or repeated/intermittent use and can be applied to the skin by spraying, painting, etc. of the adhesive.

2. State of the Art

Cyanoacrylate adhesives have been suggested for a variety of adhesive purposes including glues and adhesives for surgical treatments. In particular, cyanoacrylate adhesives of formula I:

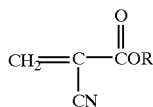

wherein R is an alkyl or other suitable substituents are disclosed in U.S. Pat. Nos. 3,527,224; 3,591,676; 3,667,472; 3,995,641; 4,035,334; and 4,650,826. Typically, when used as adhesives for treating living tissues, the R substituent is alkyl of from 2 to 8 carbon atoms and most often is butyl (e.g., n-butyl).

The suggested medical uses for cyanoacrylate adhesives include surgical environments wherein the cyanoacrylate adhesives are utilized to adhere internal tissues, repair surgical wounds and mitigate bleedings, e.g., as an alternative to sutures or as a hemostat. Typically, treatment is limited to a small defined broken skin area.

In contrast to such prior art uses of cyanoacrylate adhesives, this invention is directed to methods for inhibiting the formation of skin ulcers including, by way of example, decubitus ulcers (bedsores) and diabetic ulcers by topical application of cyanoacrylate adhesives on intact unbroken skin.

Decubitus ulcers arise from the deprivation of nutrients to the tissue arising from prolonged pressure which leads to ischemia and are common in situations were the patient remains in a fixed position for prolonged periods (e.g., long term bed or wheelchair confinement). This often occurs in tissue overlying bony prominences. However, other factors such as skin irritation (due to, for example, friction and shearing forces arising from bedding materials and clothing), moisture (bodily fluid contamination), and poor skin integrity, especially in older, compromised patients, can exacerbate and accelerate ulcer formation and skin breakdown. The effect of friction in addition reduces the amount of pressure needed for skin breakdown. When the skin becomes broken, the potential for infection and morbidity increase significantly. Care and handling of the ulcerated area become more difficult and expensive. Typically, decubitus ulcer formation is preceded by reddening of nutrient deprived skin which, with continued irritation, develops into the open bedsore (i.e., a skin ulcer).

Diabetic ulcers are formed by deprivation of nutrients to the tissue as a result of the diabetic condition including neuropathy (lack of pain sensation), poor circulation in the patient, etc. In particular, diabetic ulcer formation in nutrient deprived tissues is facilitated by skin irritation much as with decubitus ulcer formation due to, for example, bodily fluid contamination, friction, shearing forces, and poor skin integrity. Typically, diabetic ulcer formation is preceded by reddening of nutrient deprived tissue which, with continued irritation, develops into an open skin ulcer.

In any event, once formed, skin ulceration is prone to severe infection and prolonged healing. Therapies for treating skin ulcers have proven to be unsuccessful particularly in cases where the conditions causing skin ulceration remain unchanged. Accordingly, the health care industry has focused on measures to prevent the formation of skin ulcers as the best approach for treating such ulcers. In the case of decubitus ulcers, conventional prophylactic methods include, by way of example, the use of sheepskin pads, foam mattresses, specialized beds, emollients and the like. In the case of diabetic ulcers, conventional prophylactic methods include, by way of example, the use of pads in areas of nerve damage due to neuropathy (to prevent the patient from inflicting injuries to these areas due to lack of sensation), methods to enhance blood circulation in the patient, etc.

Notwithstanding such therapies, skin ulceration is a continuing and expanding problem especially with diabetic patients, bed or wheelchair ridden patients, etc. as a recent study indicates that the prevalence of pressure ulcers in hospital populations has increased by about 21% from 1989 to 1993. Meehan, *Advances in Wound Care,* Vol. 7, No. 3, pp. 27–38, 1994. Accordingly, there is an ongoing need to provide better methods for inhibiting skin ulceration and reducing the effects of pressure and irritation.

SUMMARY OF THE INVENTION

This invention is drawn to methods for inhibiting surface skin ulceration including, by way of example, decubitus ulcers (bedsores) and diabetic ulcers. The methods involve applying cyanoacrylate adhesive, particularly n-butyl cyanoacrylate adhesive, onto skin areas prone to surface skin ulceration so as to form a resilient yet flexible, waterproof polymer layer over such skin areas. In turn, this polymer layer increases the skin integrity while reducing skin irritation to the underlying skin thereby inhibiting these factors which are known to increase skin ulceration.

The methods described herein can be used by themselves to inhibit formation of surface skin ulcers, but preferably are used in conjunction with existing regimens for inhibiting formation of surface skin ulcers.

Accordingly, in one of its method aspects, this invention is directed to a method for inhibiting the formation of surface skin ulcers which method comprises:

applying to an intact skin surface area prone to ulcer formation, a sufficient amount of a cyanoacrylate adhesive so as to cover said area; and polymerizing the cyanoacrylate adhesive so as to form a flexible, waterproof, adhesive polymer coating which adheres to the area where the adhesive was applied, wherein the cyanoacrylate, in monomeric form, is represented by formula I:

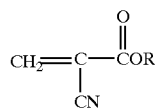

where R is selected from the group consisting of:

alkyl of 2 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

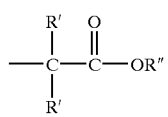

wherein each R' is independently selected from the group consisting of:

hydrogen and methyl, and

R" is selected from the group consisting of:

alkyl of from 1 to 6 carbon atoms, alkenyl of from 2 to 6 carbon atoms, alkynyl of from 2 to 6 carbon atoms, cycloalkyl of from 3 to 8 carbon atoms, aralkyl selected from the group consisting of benzyl, methylbenzyl and phenylethyl, phenyl, and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably R is alkyl of from 2 to 10 carbon atoms and more preferably alkyl of from 2 to 8 carbon atoms. Even more preferably, R is butyl or octyl and most preferably, R is n-butyl.

In a preferred embodiment, the cyanoacrylate is applied at an amount of at least 0.02 milliliter (ml), and preferably from about 0.02 to about 0.2 ml, of cyanoacrylate adhesive per square centimeter of skin which is to be covered.

In another preferred embodiment, the cyanoacrylate adhesive to be applied to the skin has a viscosity of from greater than 1 to about 100 centipoise at 20° C. More preferably, the cyanoacrylate adhesive is in monomeric form and has a viscosity of from greater than 1 to about 20 centipoise at 20° C. In still another preferred embodiment, a gel having a viscosity of up to about 50,000 centipoise or more at 20° C. can be used.

As used herein, the following terms have the following meanings:

The term "cyanoacrylate adhesive" refers to adhesive formulations based on cyanoacrylate monomers of formula I:

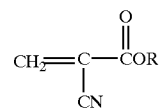

where R is selected from the group consisting of alkyl of 2 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

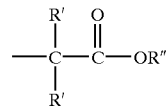

where each R' is independently selected from the group consisting of hydrogen and methyl and R" is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl or octyl and most preferably, R is n-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

A preferred cyanoacrylate adhesive for use in the invention is n-butyl-2-cyanoacrylate.

The cyanoacrylate adhesives described herein rapidly polymerize in the presence of moisture or tissue protein, and the n-butyl-cyanoacrylate is capable of bonding to human skin tissue without causing histoxicity or cytotoxicity.

DETAILED DESCRIPTION OF THE PREFERRED EMBODIMENTS

This invention relates to cyanoacrylate adhesives which are useful for inhibiting formation of surface skin ulcers. The cyanoacrylate adhesive which is applied to surface skin areas prone to ulcer formation can be monomeric or partially polymeric. In general, partially polymerized cyanoacrylate adhesives are liquid polymers having a higher viscosity than that of the corresponding monomer and, therefore, are better suited for those applications which are intended to be specific for a particular skin area. In other words, less viscous materials are more likely to "run" (i.e., flow) into areas where application was not intended.

The cyanoacrylate adhesives used herein preferably have a viscosity of from greater than 1 to about 100 centipoise and more preferably from greater than 1 to about 20 centipoise at 20° C. (e.g., for spray application). It is contemplated, however, that adhesives of higher viscosity such as pastes and gels having viscosities of up to 50,000 centipoise at 20° C. can also be employed and will make easier skin application.

The specific viscosity of the formulation depends, in part, on the amount and degree of partially polymerized cyanoacrylate adhesive employed as well as additives which are employed in the formulation to enhance or decrease viscosity. Such factors are readily ascertainable by the skilled artisan. For example, methods for preparing partially polymerized cyanoacrylate adhesives are disclosed, for example, by Rabinowitz, U.S. Pat. No. 3,527,224 which is incorporated herein by reference in its entirety. Additives which can be incorporated into the formulation to enhance its viscosity include polymers such as polymethyl methacrylate (PPMA) and polymerized cyanoacrylate adhesives as disclosed in U.S. Pat. Nos. 3,654,239 and 4,038,345 both of which are incorporated herein by reference in their entirety.

Monomeric forms of cyanoacrylate adhesives are often preferred where application is to be made to a large surface area. This preference results from the fact that those forms are less viscous and, accordingly, will permit more facile large surface area application. Mixtures of monomeric forms of cyanoacrylate adhesive and partially polymerized forms of cyanoacrylate adhesive can also be used to prepare a formulation having intermediate viscosities.

For purposes of this invention, monomeric or partially polymerized n-butyl-2-cyanoacrylate is a particularly preferred adhesive and is capable of effectively bonding to human skin tissue without causing histoxicity or cytotoxicity.

Upon contact with skin moisture and tissue protein, the cyanoacrylate adhesives will polymerize or, in the case of partially polymerized cyanoacrylate adhesives, will further polymerize, at ambient conditions (skin temperature) over about 10 to 60 seconds to provide a solid layer which forms over and strongly adheres to the surface of the skin. The resulting adhesive polymer layer or coating is flexible and waterproof thereby forming a protective barrier film (layer) which increases underlying skin integrity and reduces irritation to the surface skin area arising from shearing forces, moisture, friction, etc. In turn, increases in skin integrity and reduction in irritation inhibit formation of surface skin ulcers.

Surface skin areas prone to ulcer formation are readily identifiable to the skilled medical care provider. In a preferred embodiment, such skin areas are identified as areas of nutrient deprived and irritated skin. This latter characteristic is identified by reddening of the nutrient deprived skin. Reddening of nutrient deprived skin is viewed by the medical care provider as a likely point of skin ulceration. In another preferred embodiment, surface skin areas prone to ulcer formation correspond to skin areas over bony prominences (e.g., heels, knees, elbows, shoulders, etc.) on high risk patients as identified by conventional screening tests (e.g., the Norton scale, the Braden scale, etc.)

The cyanoacrylate adhesive is applied to provide an effectively thick coating over the human skin tissue prone to surface ulcer formation.

Generally, the cyanoacrylate adhesive provides an adhesive coating over the entire skin area prone to surface skin ulceration which, when set, is waterproof and satisfactorily flexible and adherent to the tissue without peeling or cracking. Preferably, the adhesive coating has a thickness of less than about 0.5 millimeter (mm), and more preferably the coating has a thickness of less than about 0.3 mm. In a particularly preferred embodiment, the thickness of the adhesive coating is from about 0.1 millimeter to about 0.5 millimeter and even more preferably from about 0.1 millimeter to about 0.3 millimeter.

The adhesive coating can be formed by applying at least about 0.02 ml of cyanoacrylate adhesive per square centimeter of skin, more preferably from about 0.02 to about 0.2 ml, and still more preferably from about 0.02 to about 0.1 ml, of cyanoacrylate adhesive per square centimeter of skin and yet more preferably from about 0.02 to about 0.05 ml of cyanoacrylate adhesive per square centimeter of skin.

Formulations

The cyanoacrylate adhesive formulations employed herein generally comprise monomeric and/or partially polymerized compounds of formula I described above and are sometimes referred to herein as simply cyanoacrylate adhesives. These formulations are liquid in nature and, upon contact with surface skin proteins and moisture, will polymerize to provide a solid film or layer over the skin surface.

The formulations may additionally contain one or more optional additives such as colorants, perfumes, plasticizers, anti-diffusion agents, modifying agents and stabilizers. In practice, each of these optional additives should be both miscible and compatible with the cyanoacrylate adhesive. Compatible additives are those that do not prevent the use of the cyanoacrylate adhesives for their intended use.

In general, colorants are added so that the polymerized film will contain a discrete and discernable color. Perfumes are added to provide a pleasant smell to the formulation. Stabilizers, such as sulfur dioxide, are added to minimize in situ polymerization in containers during storage. Plasticizers, such as dioctylphthalate or tri(p-cresyl) phosphate, are added in order to enhance the flexibility of the resulting polymer layer. Each of these additives is conventional. For example, suitable stabilizers are disclosed in U.S. Pat. No. 4,650,826 and suitable plasticizers are disclosed in U.S. Pat. Nos. 2,784,127 and 4,444,933, the disclosures of which are incorporated herein by reference in their entirety.

The amount of each of these optional additives employed in the cyanoacrylate adhesive is an amount necessary to achieve the desired effect.

The formulation is generally stored in an applicator for use in a single dose application (e.g., a disposable container) or for use in repeated applications. Single dose applicators include those having breakable or removable seals that prevent moisture, including atmospheric moisture, from contacting the formulation and causing premature in situ polymerization.

For repeated and intermittent usage, minimal exposure to atmospheric moisture is required. This can be achieved by devices having very narrow outlets and low initial dead space. One applicator for such repeated intermittent use is described in U.S. Pat. No. 4,958,748 which is incorporated herein by reference in its entirety.

Another applicator comprises a conventional spray applicator wherein the cyanoacrylate adhesive is sprayed onto the surface skin area prone to ulceration. The spray rate of the applicator can be controlled so that application of a metered quantity of adhesive per unit area of skin surface over a set period of time is controlled.

Still another applicator comprises a brush or solid paddle applicator wherein the cyanoacrylate adhesive is "painted" onto the surface skin area prone to skin ulceration.

A preferred applicator for repeated and intermittent usage is an applicator suitable for the non-sterile storage and metered dispersement of a cyanoacrylate adhesive after opening of the applicator wherein the applicator is characterized as having a resealable opening of no more than about 0.05 square inch (0.323 square centimeters) so as to permit the metered dispersement of the adhesive from the applicator and which is capable of multiple administrations of the adhesive and is further characterized as having resealing means such as a cap which either tightly mates with the applicator or which screws onto the applicator.

Preferably, the opening of the applicator is about 0.001 to about 0.01 square inch (about 0.00645 to about 0.0645 square centimeters).

In another preferred embodiment, the walls of the applicator are made of a pliable material, so that upon application of pressure onto the walls, the walls depress sufficiently to force the adhesive contained in the applicator through the opening. In still another preferred embodiment, the adhesive is released from the applicator by a gravity feed methods well known in the art. Such methods do not require application of pressure to the walls of the container.

Preferably, the applicator is manufactured with its opening covered by a metal foil or other similar construction which closes this opening until the device is ready for use. The opening is then reinstated by use of a pin or similar device which punctures the covering.

Such devices for intermittent use enable multiple uses of the cyanoacrylate adhesive at different points in time by the same or different individuals.

In applicators suitable for repeated intermittent uses, the cyanoacrylate adhesive is stored at ambient conditions and is selected to be bacteriostatic. See, for example, Rabinowitz et al., U.S. Pat. No. 3,527,224. When the selected adhesive is bacteriostatic, prolonged storage at ambient conditions can be achieved without regard to the sterility of the formulation because there is no adverse buildup of bacteria during storage.

Methodology

The above-described formulations are applied to unbroken surface skin areas prone to ulceration under conditions suitable for polymerizing the adhesive so as to form a protective coating and typically under non-sterile conditions. In general, sufficient amounts of cyanoacrylate adhesive are employed to cover (i.e., coat) the entire surface skin area prone to ulceration (e.g., the entire reddened area in nutrient deprived skin). The coating is preferably extended by at least about 1 centimeter and preferably by at least about 5 centimeters beyond the surface skin area prone to ulceration (e.g., beyond the reddened area described above). However, application to broke skin is preferably avoided.

The adhesive polymer coating should be maintained in a unbroken manner over the entire skin area prone to ulceration. This can be assured by careful application of the adhesive onto the skin. Additionally, the use of a plasticizer will facilitate the maintenance of the polymer coating in an unbroken manner. However, to further ensure that the polymer coating is maintained unbroken, after the initial layer of adhesive has cured to provide for an adhesive polymer coating, a second, preferably thinner, layer is preferably applied over the adhesive polymer coating. Additional amounts of cyanoacrylate adhesive can be applied as needed to maintain an unbroken callous like covering over the ulcer prone surface skin areas.

Sufficient cyanoacrylate adhesive is preferably employed to form a coating of less than about 0.5 mm thick and more preferably at least about 0.1 mm thick. Such coatings can be formed by applying, for example, about 0.02 ml of cyanoacrylate adhesive per square centimeter of skin surface area.

The amount of cyanoacrylate adhesive applied onto the skin surface area can be controlled by the amount of adhesive packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the adhesive in a controlled drop wise manner. Other methods for the controlled dispersement of the cyanoacrylate adhesive are as described above including, by way of example, a conventional spray applicator, a brush or solid paddle applicator, and the like.

Upon application of the cyanoacrylate adhesive, the surface skin moisture, tissue protein, and temperature are sufficient to initiate polymerization of the adhesive upon application. Thereafter, the skin surface is maintained under suitable conditions to allow polymerization to proceed to formation of an adhesive coating.

In general, the particular length of time required for polymerization will vary depending on factors such as the amount of adhesive applied, the temperature of the skin, the moisture content of the skin, the surface area of skin for adhesive application, and the like. However, in a preferred embodiment, polymerization is generally complete within about 10 to about 60 seconds while the skin is maintained at ambient conditions. During this period, the person to whom application of the cyanoacrylate adhesive has been made merely allows the adhesive to form a coating while minimizing any action to prevent the adhesive from being dislodged from that portion of the skin where it was applied or to adhere to unintended objects. Excess adhesive polymer can be removed with acetone (nail polish remover) which can be readily conducted except in the case where the adhesive polymer binds to a sensitive skin part (e.g., the eye lids) where it should be removed by a health care professional.

After the adhesive coating has formed, the coating strongly adheres to the skin, is flexible and waterproof, thereby forming a protective coating which enhances the integrity of the underlying skin and protects the skin from further irritation thereby retarding or inhibiting surface skin ulceration.

In general, the coating will adhere to the skin for a period of about 1–3 days after which time it sloughs off. Additional applications can be made if desired.

Because the cyanoacrylate adhesive polymer coating is waterproof, the patient is not prevented from bathing and other activities involving exposure to water during the period the adhesive layer protects this skin area.

The following examples illustrate certain embodiments of the invention but is not meant to limit the scope of the claims in any way.

EXAMPLES

Example 1

A cyanoacrylate adhesive formulation is prepared in monomeric form using n-butyl α-cyanoacrylate and which contains a colorant to readily ascertain where the formulation has been applied, 20 weight percent of dioctyl phthalate which acts as a plasticizer to enhance the flexibility of the resulting polymer composition, and 200 parts per million (ppm) of sulfur dioxide which acts as a stabilizer. The formulation is applied onto an approximately 50 square centimeter nutrient deprived and irritated skin area prone to surface skin ulceration which, in this case, is prone to decubitus ulcer formation on the buttocks of a bed ridden human male patient as evidenced by reddening of this skin indicating irritation. The formulation is applied at the rate of 0.03 milliliter per square centimeter of treated skin. Application is made by use of a latex gloved finger or by use of a finger cot. After application, the skin is maintained at ambient condition until a polymer coating forms in about 30 to 60 seconds. After the polymer coating has formed, preventive methods to inhibit decubitus ulcer formation in the patient, including, sheepskin pads, specialized beds, patient rotation and the like, are continued.

In this regard, the application of the cyanoacrylate adhesive polymer layer to the skin area prone to decubitus ulcer formation in conjunction with other conventional therapies to prevent decubitus ulcer formation will reduce the incidence of decubitus ulcer formation as compared to treatments involving conventional therapies without application of the adhesive polymer layer.

Example 2

A cyanoacrylate adhesive formulation is prepared in monomeric form using n-butyl α-cyanoacrylate and which contains a colorant to readily ascertain where the formulation has been applied, 20 weight percent of dioctyl phthalate which acts as a plasticizer to enhance the flexibility of the resulting polymer composition, and 200 parts per million (ppm) of sulfur dioxide which acts as a stabilizer. The formulation is applied onto an approximately 20 square centimeters nutrient deprived and irritated skin area prone to surface skin ulceration which, in this case, is prone to diabetic ulcer formation on the foot of a human female patient as evidenced by reddening of this skin indicating irritation. The formulation is applied at an amount of 0.03 milliliter per square centimeter of treated skin and, after application, the skin is maintained at ambient condition until a polymer coating forms in about 30 to 60 seconds. After the polymer coating has formed, preventive methods to inhibit diabetic ulceration in this patient, including, the use of pads, specialized footwear, methods to enhance blood circulation in the patient, and the like, are continued.

In this regard, the application of the cyanoacrylate adhesive polymer layer to the skin area prone to diabetic ulceration in conjunction with other conventional therapies to inhibit diabetic ulceration will reduce the incidence of diabetic ulceration as compared to treatments involving conventional therapies without application of the adhesive polymer layer.

Example 3

An evaluation of the effect of n-butyl cyanoacrylate adhesive on the inhibition of decubitus ulcers in 17 adult patients located in nine different nursing homes was conducted. In this example, 17 patients were selected based on a history of recurring decubitus ulcer formation or, based on medical evaluation, were deemed to be at high risk of developing decubitus ulcers. A prophylactic treatment regimen was then employed on these patients which regimen consisted of using conventional pressure ulcer preventative practices primarily involving periodic rotation of the patient as well as application of an n-butyl cyanoacrylate adhesive composition onto the intact skin areas which appeared likely to develop pressure ulcers by virtue of irritation and reddening of the skin or unbroken blister formation which is classified as a stage I decubitus ulcer or by application of the n-butyl cyanoacrylate composition onto intact skin adjacent to type II decubitus ulcers. Application of n-butyl cyanoacrylate consisted of application of about 1–5 drops of the n-butyl cyanoacrylate composition onto the surface skin area prone to ulceration wherein each drop corresponds to about 0.03 ml of cyanoacrylate.

The specific amount of n-butyl cyanoacrylate adhesive and point of application of the adhesive for each patient are set forth in the following Table I:

TABLE I

APPLICATION OF N-BUTYL CYANOACRYLATE ADHESIVES
TO PATIENTS TO INHIBIT DECUBITUS ULCER FORMATION

| NURSING HOME | PATIENT NUMBER | WHERE | TYPE OF IRRITATION | SIZE | AVE. NUMBER OF DROPS |
|---|---|---|---|---|---|
| A | 1 | Heel | Redness | 3 cm | 2 |
| A | 2 | Heel | Redness | 3 cm | 2 |
| B | 3 | Heels (2) | Blister (Stage I) | 3–4 cm | 2 |
| B | 4 | Heels (2) | Redness | 3–5 cm | 2 |
|   |   | Elbows (2) | Redness | 3–5 cm | 2 |
| C | 5 | Cheek | Redness | ½–3 in | 2 |
| C | 6 | Lower Leg | Bruise | 2–3 in | 4–5 |
| D | 7 | Shoulder | Bony Prominence | 3–4 cm | 3–4 |
| D | 8 | Hip | Bony Prominence | 3–4 cm | 3–4 |
| E | 9 | Heels (2) | Redness | 5 cm | 1 |
| E | 10 | Hip | Blister (Stage I) | 3–4 cm | 2 |
| E | 11 | Top of Foot | Redness | 2–5 cm | 1 |
| F | 12 | Heel | Redness (Scabbed over - healed stage II) | 6–8 cm | 3 |
| G | 13 | Knees & Heels | Redness | 2.5 cm | 3 |
| G | 14 | Heel | Skin Redness around Stage II ulcer | 2.5 cm | 3 |

TABLE I-continued

APPLICATION OF N-BUTYL CYANOACRYLATE ADHESIVES
TO PATIENTS TO INHIBIT DECUBITUS ULCER FORMATION

| NURSING HOME | PATIENT NUMBER | WHERE | TYPE OF IRRITATION | SIZE | AVE. NUMBER OF DROPS |
|---|---|---|---|---|---|
| G | 15 | Heels (2) | Redness | 2.5 cm | 3 |
| H | 16 | Hip | Redness (healed Stage II ulcer) | 2 cm | 2–3 |
| I | 17 | Gluteal Fold | Stage I area around stage II | 3–3.5 cm | 3–4 |

After application, the cyanoacrylate adhesive was allowed to form a polymeric film and, on average, reapplication of the adhesive was conducted every 24 hours until the evaluation was completed.

As a result of this evaluation, all patients treated with conventional pressure ulcer preventative practices as well as n-butyl cyanoacrylate adhesive having either redness/irritation of intact skin or having blistering of intact skin characterized as stage I decubitus ulcer formation did not progress to stage II decubitus ulcer formation characterized by broken skin. Moreover, all patients treated with conventional pressure ulcer preventative practices as well as n-butyl cyanoacrylate adhesive in skin areas adjacent to stage II decubitus ulcer formation showed minimal expansion of the ulcer to the adjacent skin areas. The specific results documented for each of the seventeen patients regarding the use of the n-butyl cyanoacrylate adhesive are set forth in Table II below:

TABLE II

RESULTS OF APPLICATION OF N-BUTYL
CYANOACRYLATE ADHESIVES TO PATIENTS
TO INHIBIT DECUBITUS ULCER FORMATION

| PATIENT NO. | RESULT |
|---|---|
| 1 | NO BREAKDOWN OF SKIN ON HEEL |
| 2 | LESS PERSPIRATION AND NO IRRITATION |
| 3 | NO BREAKDOWN OF BLISTER TO STAGE II DECUBITUS ULCER |
| 4 | NO SKIN BREAKDOWN ON HEELS OR ELBOWS |
| 5 | NO IRRITATION DEVELOPED |
| 6 | ABSORPTION OF BRUISE WITH NO SKIN BREAKDOWN |
| 7 | NO IMPROVEMENT/NO CHARGE BUT SKIN DID NOT BREAKDOWN |
| 8 | NO SKIN BREAKDOWN |
| 9 | NO IRRITATION/REDDENING LEFT |
| 10 | WARMING SENSATION UPON APPLICATION - TREATMENT STOPPED |
| 11 | NO IRRITATION/REDDENING LEFT |
| 12 | REDNESS HEALED UP |
| 13 | IRRITATION IMPROVED BUT PATIENT PASSED AWAY DUE TO OTHER CONDITIONS |
| 14 | NO IRRITATION EVIDENT - HEELS ALMOST HEALED |
| 15 | PATIENT'S HEELS LOOK BETTER, ALMOST TOTALLY HEALED |
| 16 | NO FURTHER BREAKDOWN, REDDENING STILL THERE BUT PROGRESSION SEEMS TO HAVE STOPPED |
| 17 | AREA IS RESOLVED, NO OPEN STAGE II'S AND STAGE I ALMOST GONE (NO REDNESS) |

The above results illustrating the failure of any patient to progress to stage II decubitus ulcer evidences the fact that the application of cyanoacrylate adhesive in conjunction with conventional pressure ulcer preventative practices inhibits decubitus ulcer formation.

From the foregoing description, various modifications and changes in the composition and method will occur to those skilled in the art. All such modifications coming within the scope of the appended claims are intended to be included therein.

What is claimed is:

1. A method for inhibiting the formation of surface skin ulceration characterized by either decubitus ulcers or diabetic ulcers in a patient which method comprises:

identifying an unbroken, uninfected, unwounded skin surface area prone to decubitus or diabetic ulceration;

applying to said unbroken, uninfected, unwounded skin surface area prone to said ulceration a sufficient amount of a cyanoacrylate adhesive so as to cover said area; and polymerizing the cyanoacrylate adhesive so as to form a flexible, waterproof, adhesive polymer coating which adheres to the area where the adhesive was applied, wherein the cyanoacrylate, in monomeric form, is represented by formula I:

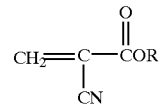

I where R is selected from the group consisting of:

alkyl of 2 to 10 carbon atoms, alkenyl of from 2 to 10 carbon atoms, cycloalkyl groups of from 5 to 8 carbon atoms, phenyl, 2-ethoxyethyl, 3-methoxybutyl, and a substituent of the formula:

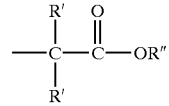

wherein each R' is independently selected from the group consisting of:

hydrogen and methyl, and

R" is selected from the group consisting of:

alkyl of from 1 to 6 carbon atoms, alkenyl of from 2 to 6 carbon atoms, alkynyl of from 2 to 6 carbon atoms, cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

2. A method according to claim 1 wherein R is alkyl of from 2 to 10 carbon atoms.

3. A method according to claim 2 wherein R is butyl or octyl.

4. A method according to claim 3 wherein R is n-butyl.

5. A method according to claim 1 wherein said adhesive is applied so as to provide at least 0.02 ml of cyanoacrylate adhesive per square centimeter of skin which is to be covered.

6. A method according to claim 5 wherein the cyanoacrylate adhesive is applied so as to provide from about 0.02 ml to about 0.2 ml per square centimeter of skin which is to be covered.

7. A method according to claim 6 wherein the cyanoacrylate adhesive is applied at an amount of from about 0.02 ml to about 0.05 ml per square centimeter.

8. A method according to claim 1 wherein the cyanoacrylate adhesive has a viscosity of from greater than 1 to about 100 centipoise at 20° C.

9. A method according to claim 8 wherein the cyanoacrylate adhesive has a viscosity of from greater than 1 to about 20 centipoise at 20° C.

10. A method according to claim 1 wherein the cyanoacrylate adhesive is applied from a single use disposable applicator.

11. A method according to claim 1, wherein the cyanoacrylate adhesive is applied from a multiple, intermittent use applicator.

12. A method according to claim 1 wherein said ulcers are decubitus ulcers.

13. A method according to claim 1 wherein the surface skin ulcers are diabetic ulcers.

* * * * *